United States Patent [19]

Boag

[11] Patent Number: 4,695,385
[45] Date of Patent: Sep. 22, 1987

[54] DIALYZER REUSE SYSTEM

[75] Inventor: James T. Boag, Evergreen, Colo.

[73] Assignee: Colorado Medical, Inc., Evergreen, Colo.

[21] Appl. No.: 728,204

[22] Filed: Apr. 29, 1985

[51] Int. Cl.[4] .......................... B01D 13/01; B08B 3/04
[52] U.S. Cl. .................................. 210/636; 210/138; 210/141; 210/143; 210/321.3; 210/424; 210/746; 210/764; 210/765; 134/18; 134/22.12; 422/28
[58] Field of Search .................. 422/28; 134/18, 25.1, 134/22.11, 22.12, 22.17, 22.13, 57 R, 95; 210/138, 141, 143, 195.2, 321.1, 321.2, 321.3, 321.4, 424, 636, 746, 764, 765, 805, 927, 139

[56] References Cited

U.S. PATENT DOCUMENTS

| 3,342,328 | 9/1967 | Swenson | 210/321.3 |
| 3,441,136 | 4/1969 | Serfass et al. | 210/138 X |
| 3,753,493 | 8/1978 | Mellor | 210/140 |
| 3,871,913 | 3/1975 | Shaldon | 210/321.3 X |
| 3,920,030 | 11/1925 | Mason | 134/58 R |
| 4,153,554 | 5/1979 | von der Heide et al. | 210/137 X |
| 4,166,031 | 8/1979 | Hardy | 210/96.2 X |
| 4,332,264 | 6/1982 | Gortz et al. | 210/140 X |
| 4,444,596 | 4/1984 | Gortz et al. | 134/18 |
| 4,444,597 | 4/1984 | Gortz et al. | 134/18 |
| 4,517,081 | 5/1985 | Amiot et al. | 210/140 X |

OTHER PUBLICATIONS

Simultaneous Reprocessing of Hollow Fiber Dialyzers and Blood Tubing Sets for Multiple Use by David A. Ogden, pp. 366–375, Published in Dialysis & Transplantation, vol. 13, No. 6, Jun., 1984.

Primary Examiner—Richard V. Fisher
Assistant Examiner—W. Gary Jones
Attorney, Agent, or Firm—James E. Pittenger

[57] ABSTRACT

A dialysis reuse system for cleansing, sterilizing and testing a hemodialysis machine and its associated dialyzer and blood tubing set. The reuse control device automatically controls either the selected reuse cycle or dialyzer test cycle as desired. In the reuse cycle a proper solution of bleach, rinse water and formaldehyde disinfectant is flushed through the system for a prearranged time period and in proper sequence to completely cleanse and disinfect the entire dialysis system including the dialyzer and blood lines. At the end of the cycle, the system is isolated, leaving the disinfectant solution intact within the system to prevent bacteria growth and contamination. In the dialyzer test cycle, a dialyzer clearance test is automatically performed using the associated hemodialysis machine to test the condition of the dialyzer membrane prior to patient treatment. The adapter valve allows the cleaning solution to be reversed through the blood side of the dialyzer, allowing momentary reversals to dislodge and remove any blood clots or other matter which may be present in the system. The fluid from the reuse device is drawn into the dialysis machine at a vacuum point in the dialysate tubing which also allows air to be removed from the reuse output fluid as well as causing the solutions to mix completely to obtain proper dilution. Conductivity testing of the fluids used in the system is periodically performed to verify that the proper solutions are present during the cleansing and disinfecting cycle as well as the clearance test performed for characterization of the dialyzer.

12 Claims, 20 Drawing Figures

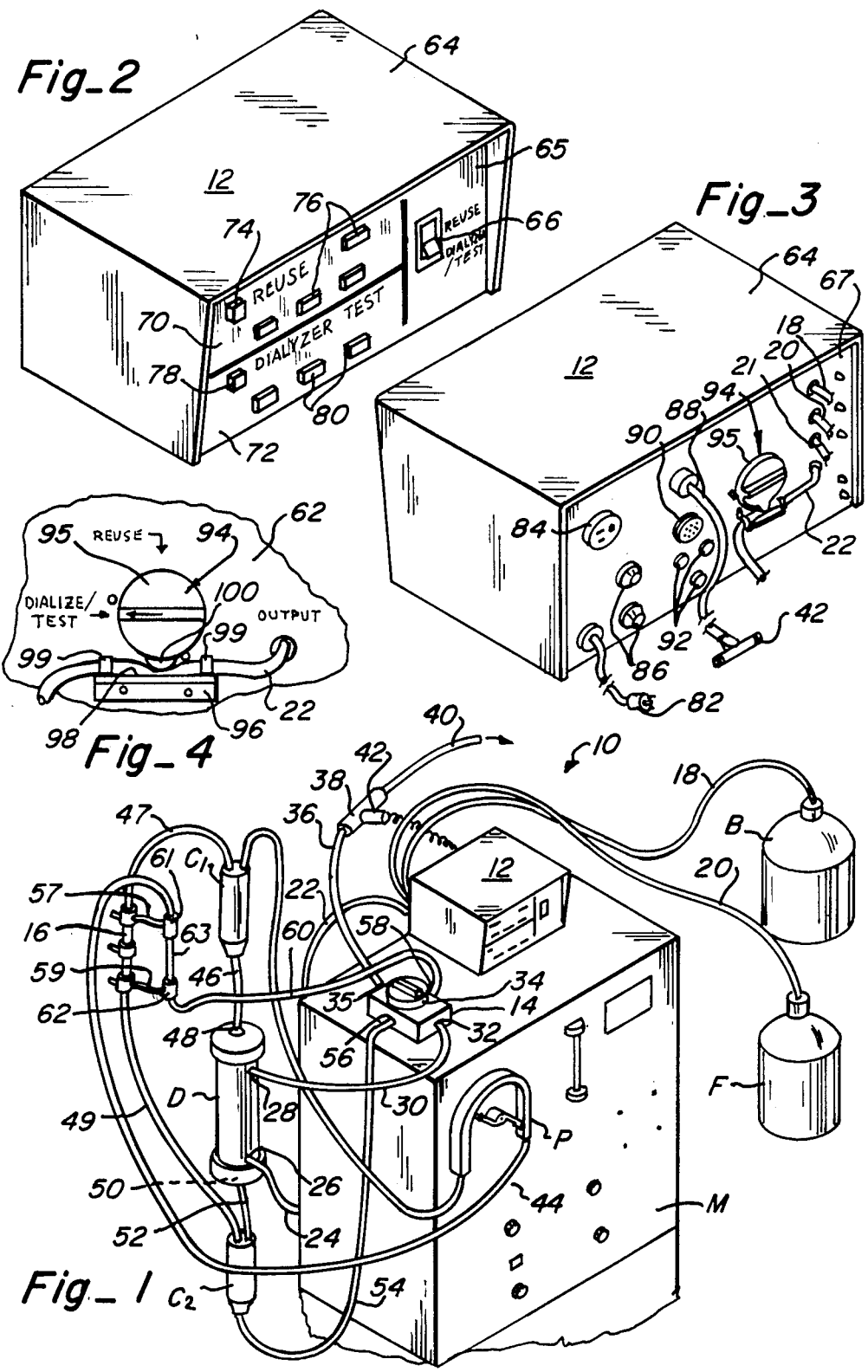

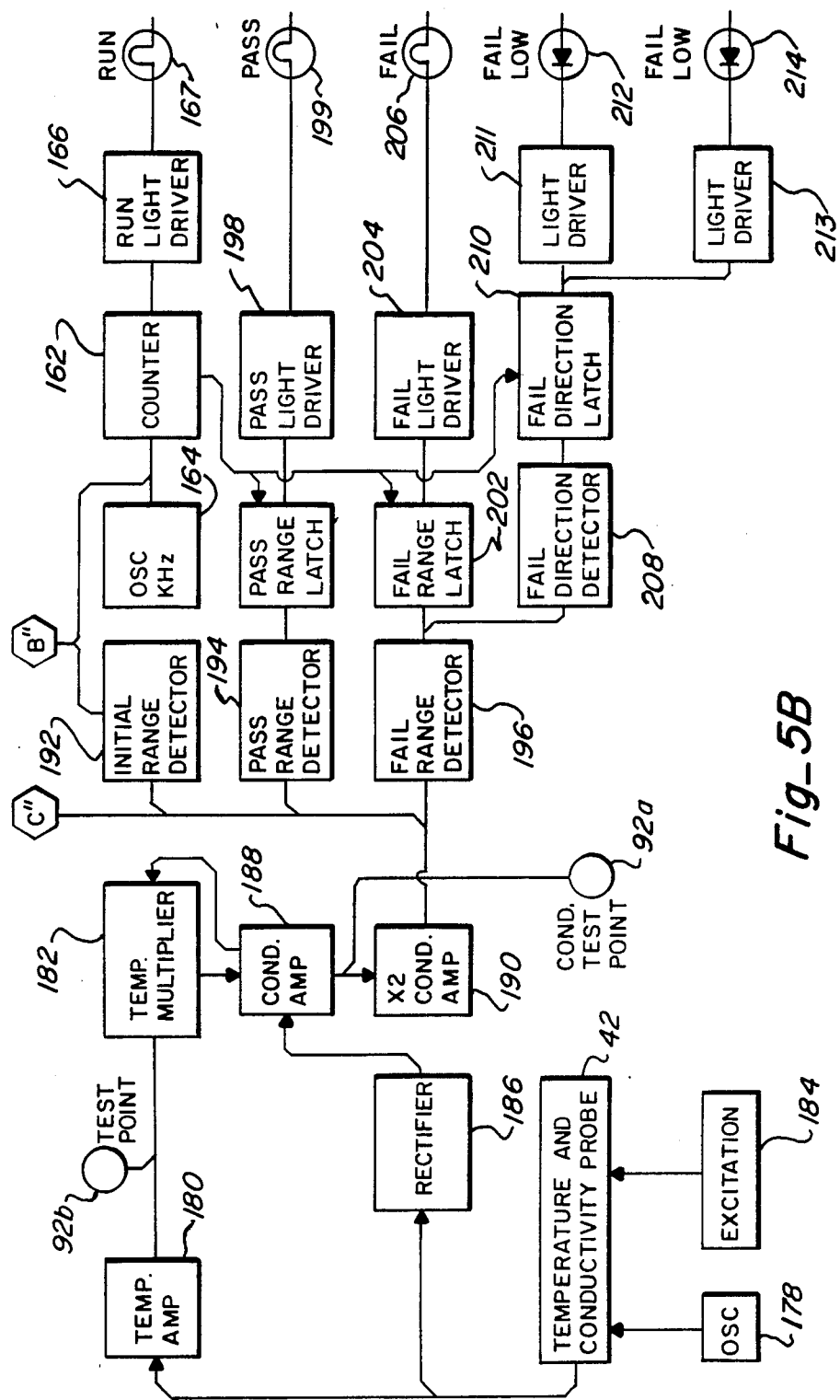
Fig_5B

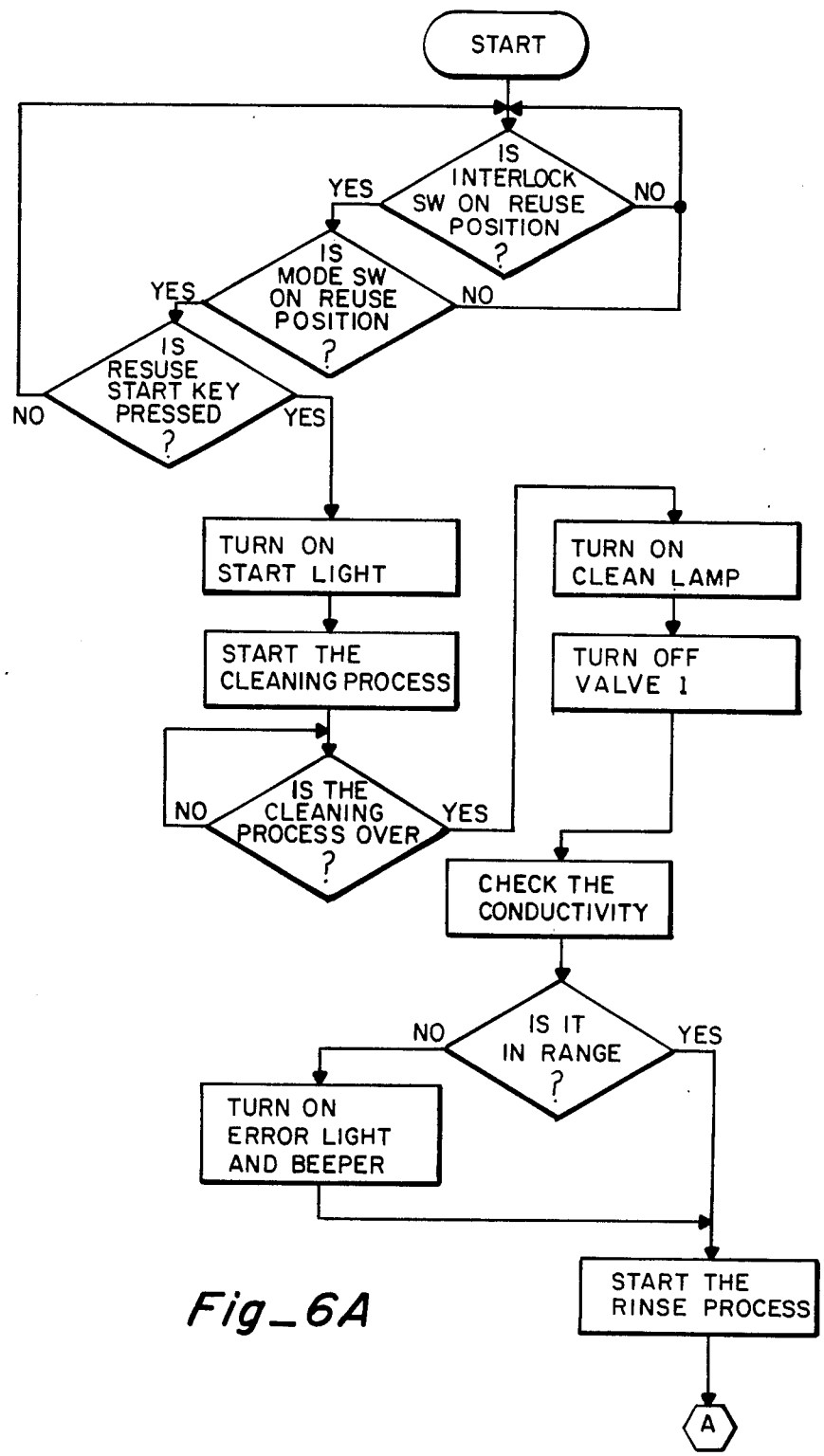
Fig_6A

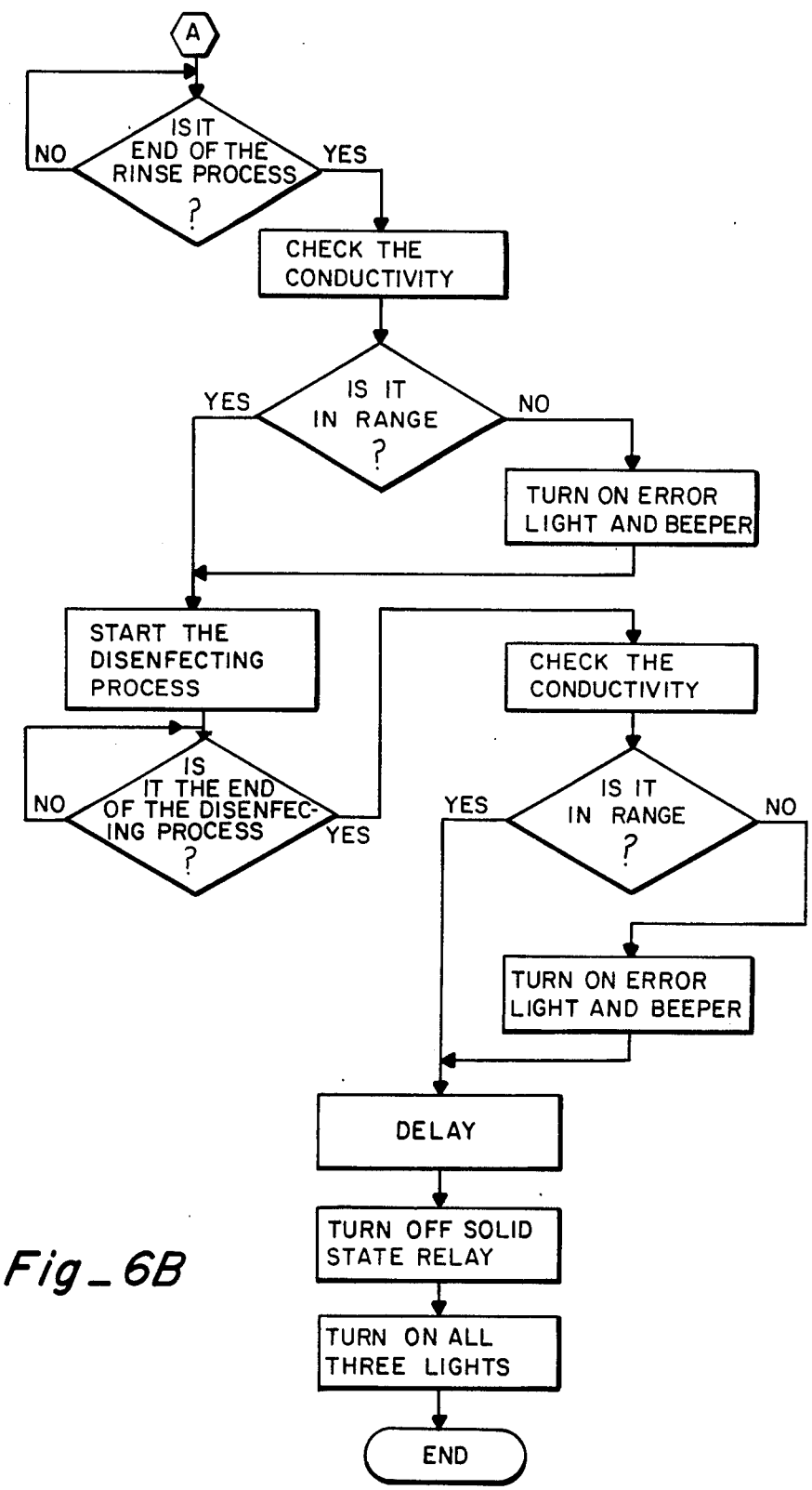
Fig_6B

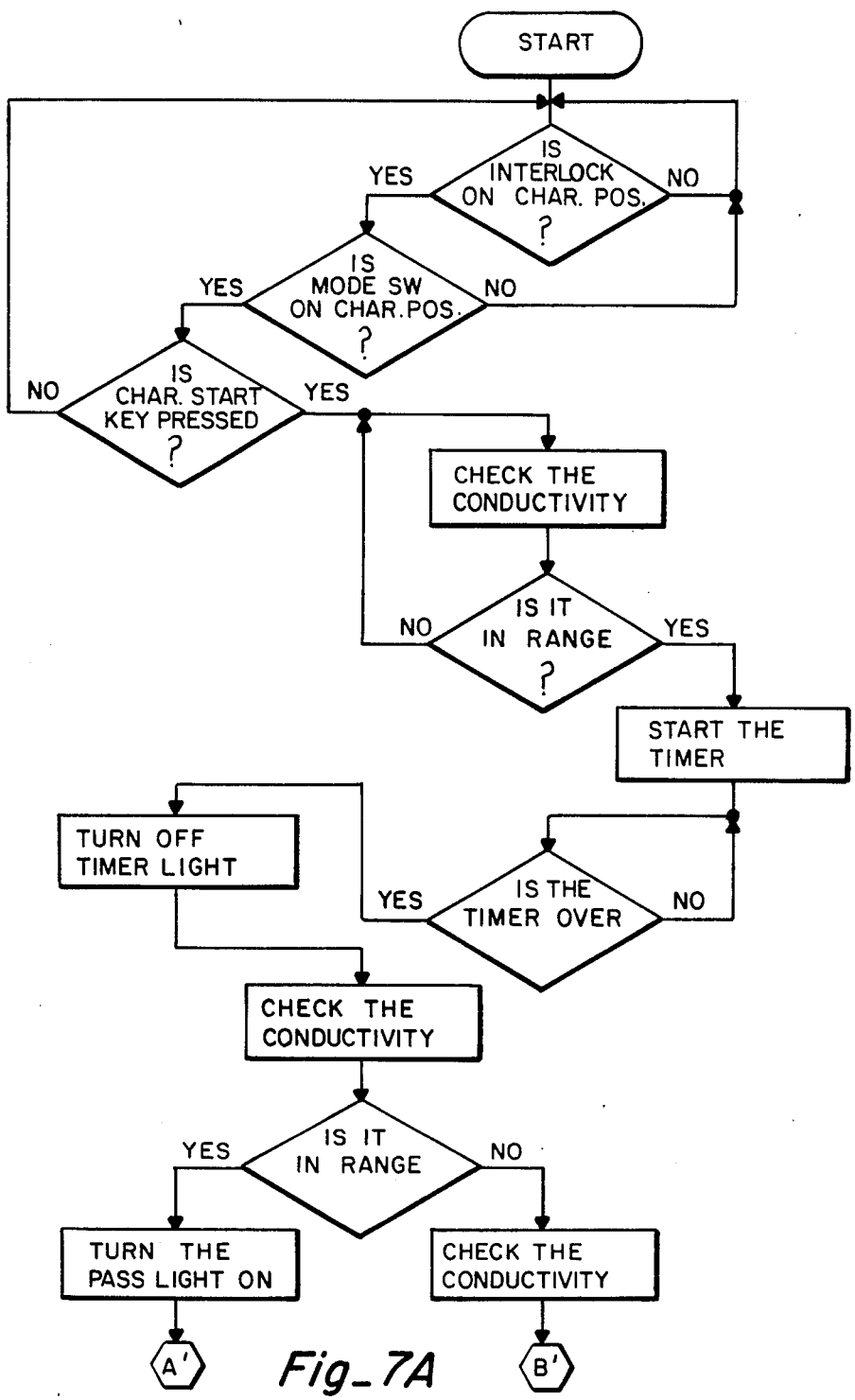
Fig_7A

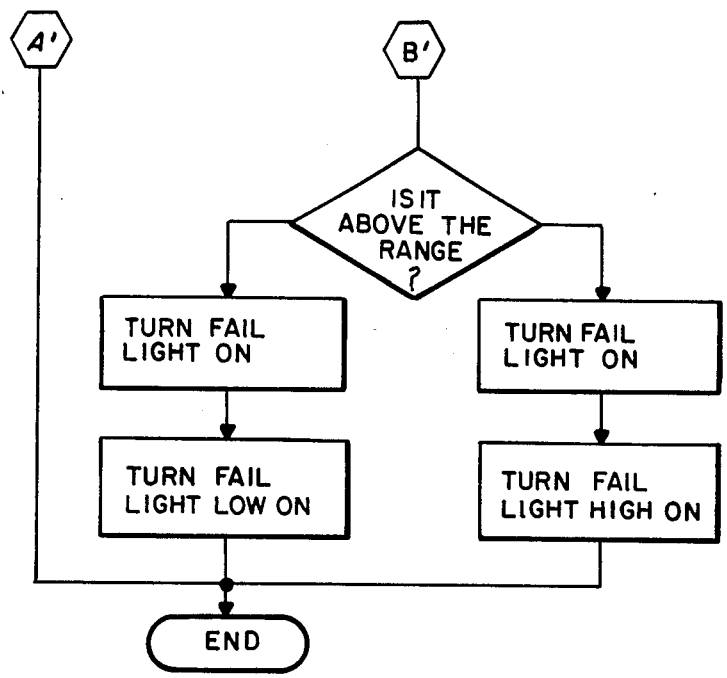
Fig_7B

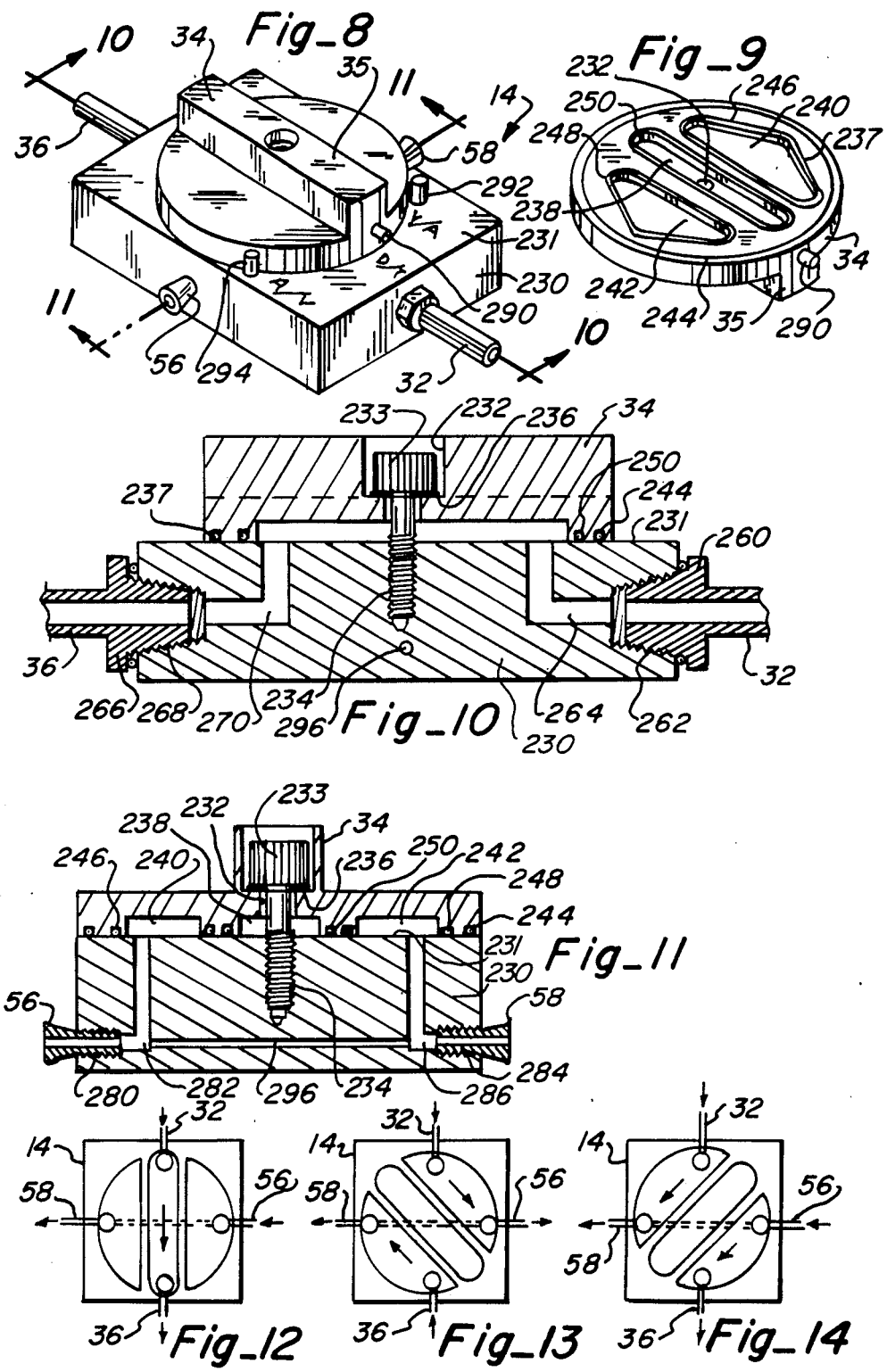

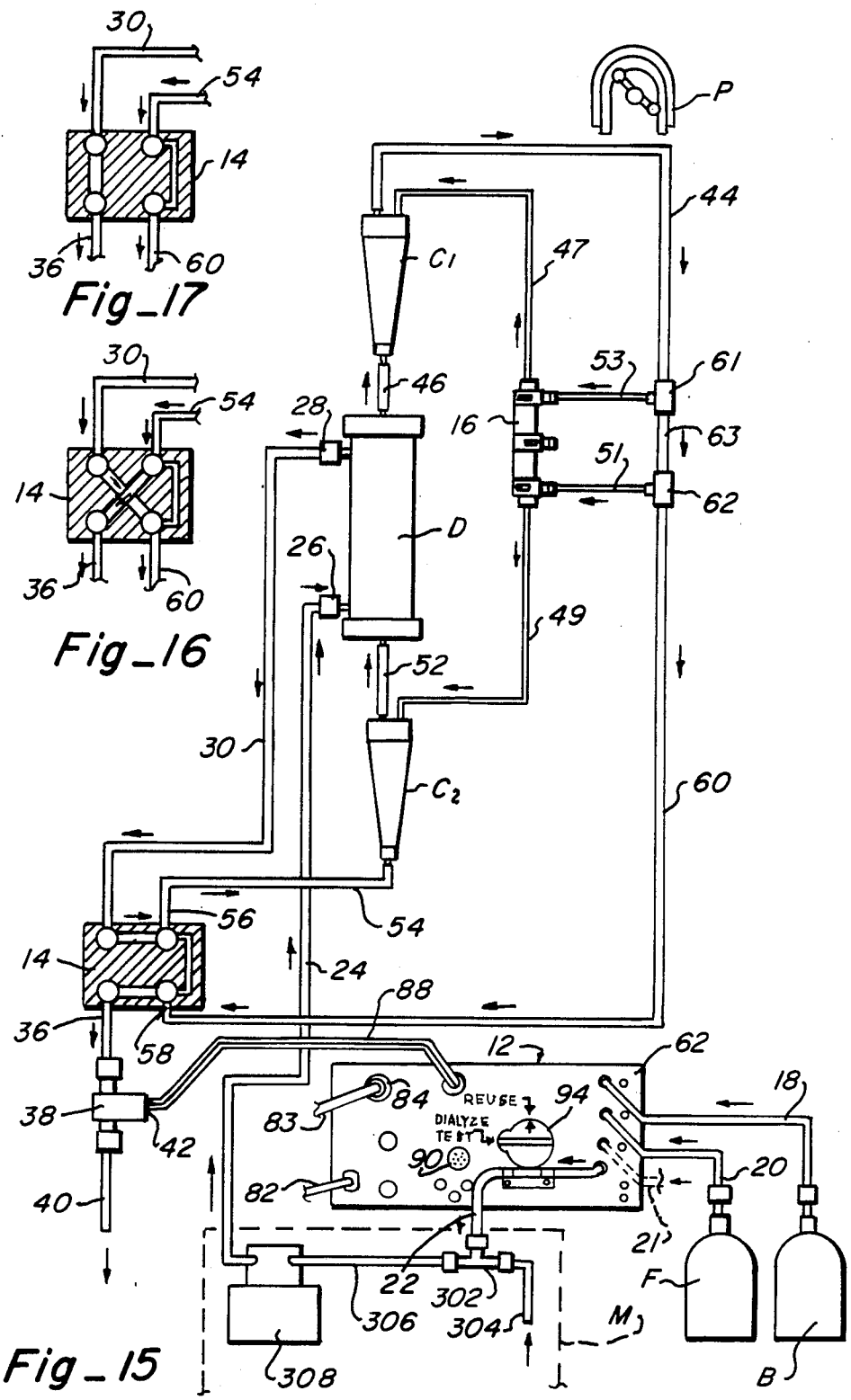

DIALYZER REUSE SYSTEM

FIELD OF THE INVENTION

This invention is directed to a system for cleaning and disinfecting a disposabl=dialyzer used in conjunction with various hemodialysis machines. It is more specifically directed to a system including an automated reuse device, fluid adapter valve and blood tubing manifold for completely cleaning and disinfecting the blood tubes and dialyzer used repeatedly with a hemodialysis machine.

BACKGROUND OF THE INVENTION

In the past, humans have experienced a situation wherein their kidneys no longer function to purify their blood because of disease, permanent injury or surgical removal of bo kidneys. Thus, when kidney failure occurs, an accumulation of toxic wastes in the patient's blood results in eventual death from uremic poisoning unless these wastes can be removed by some artificial method or device.

Hemodialysis has been well known as a means for circulating a patient's blood on one side of a membrane which has "minute pores" through which waste products from the blood may pass but which are too small to permit blood cells and protein to be lost. A dialysis fluid generated by e hemodialysis machine is circulated on the opposite side of the membrane to flush and remove these waste products as they are dissipated. As is common practice in hemodialysis treatment, the patient's blood is passed through the dialyzer for various periods of time up to six hours with this type of treatment repeated several times each week. Various critical problems occur in the use of this type of treatment in that the dialyzer and the hemodialysis machine must be cleaned and disinfected after each use to prevent contamination and complications to the patient.

With the old type dialyzers and hemodialysis machines, it was necessary to manually clean and flush the dialyzer and associated tubing with a subsequent sterilization process following. Since this required the use of trained technicians to perform this service, in most cases the treatment could take place only at hospitals or dialysis treatment centers, with very little of this treatment performed at the patient's home.

In the early 1970's, a major step was taken in that the dialyzer was improved and perfected in a disposable form that was considerably cheaper than the previous dialyzers used. Even in this new disposable form, the dialyzer costs average between $25 and $35. Because these dialyzers are intended to be disposable, they eliminate the problems connected with the cleaning and sterilizing of the dialyzer before subsequent use. However, because of the relatively high cost of the disposable dialyzer and, in addition, the cost of the blood tube set that is required to be used with the dialyzer, the expense of the individual treatments to the patient is still quite high primarily because of the required continuing treatment.

With the continued use of the disposable dialyzers, an attempt was made to develop a procedure for reusing the dialyzer more than once in order to effect a much more economical treatment schedule for the patient.

In the prior art various attempts have been made to develop suitable reuse machines which could be utilized in conjunction with the hemodialysis machines to automatically clean, flush and disinfect the disposable dialyzer and blood lines and the hemodialysis machine. With the development of these devices, it became more feasible for the individual patients to treat themselves in the privacy of their own homes. In this way, the costs are considerably reduced, not only because the equipment can be reused but also due to the fact that highly skilled technicians are no longer required with their attendant costs.

These prior art reuse devices have suffered on many occasions from various shortcomings such as leakage at various fittings, corrosion of metal parts used within the system, inability to be used with more than one type of artificial kidney or dialyzer, and the inability to adjust the cleaning and disinfecting cycles to fit various time needs. Thus, these shortcomings produced major problems in that there was always a risk of contamination with the inability to properly test the dialyzer and system so that only competent dialyzers and blood tubing sets would ever be reused.

In addition to the above background discussion, it is interesting to note that various research studies have been performed to determine if there is a difference in patient mortality related to the multiple use of dialyzers as compared to single use. As a result of this research, it has been found that there are significant benefits obtainable by the multiple use of the dialyzer. It was shown as a matter of course that two primary patient symptoms, namely, back pain and chest pain, were markedly reduced with the use of reprocessed dialyzers. In addition, the reused dialyzers also showed a far superior bio-compatibility to that of the new dialyzers.

Within recent time the medical profession has begun to standardize procedures for reuse of dialyzers. In establishing these standards, four major problem areas have been identified. These areas are: (1) membrane transfer efficiency, (2) mechanical competency of the dialyzer and blood lines, (3) chemical contamination and (4) bacteriological safety. The characteristic of the dialyzer which is of utmost importance is its ability to transfer dissolved solutes. One test which is provided to determine the effectiveness of the dialyzer to transfer solutes is the "clearance" test. This test verifies the mass transfer efficiency and the mechanical integrity of the dialyzer and therefore covers the first two major problem areas which are of concern.

An additional problem that has confronted many users of hemodialysis machines and reuse has been the exposure to chemicals used in the cleaning and disinfecting process. The chemicals currently being used to recondition dialyzers include hypochlorites, iodoforms, hydrogen peroxide, peracetic acid, formaldehyde, glutaraldehyde and various combinations of these groups. Because of their high concentrations, these chemicals can pose potential health problems. The use of these chemicals indiscriminately have made it difficult for an individual person to manually reuse and clean the dialyzers, thus setting up the necessity for automatic reuse devices. As a result of these problems, it has been recognized that it is important to provide a closed system to eliminate any fumes and the exposure of the user or patient to these chemicals during the reuse process.

The last area of concern requires that the dialyzer, blood tubing set and hemodialysis machine be properly disinfected and allowed to remain in a sealed condition during storage and prior to the next dialysis treatment. This has been a characteristic problem of many of the older prior art reuse devices in that tubing, dialyzer and equipment connections must be broken and made with the integrity of the overall system violated with the possibility of chemical, air or bacteria contamination being introduced.

As a response to these four major concerns, the present invention was developed as a means for vastly improving the reuse cycle for the dialyzer and blood tubing sets in order to improve and correct the various deficiencies which have been noted in the prior art devices and systems.

INFORMATION DISCLOSURE STATEMENT

The following information refers to the most pertinent prior art of which the applicant is aware with respect to the subject matter of the present invention. This statement is believed to comply with the applicant's acknowledged duty to inform the Patent and Trademark Office of any pertinent information which is material to the examination of this application.

The Shaldon patent (U.S. Pat. No. 3,871,913) discloses a system for supplying a blood dialyzer with dialyzing fluid and connections enabling the system to be connected with the dialysate and blood compartments in parallel after a dialysis treatment. The dialysate supply system is used to supply washing and sterilizing liquids both to the blood chamber and dialysis chamber of the dialyzer simultaneously during the reuse process.

The Mellor patent (U.S. Pat. No. 3,753,493) discloses a cleaning apparatus for artificial kidneys or dialyzers. The device provides automatic cleaning and sterilizing of the dialyzer through an automatic arrangement of solenoids, valves and timer. A parate receptacle is provided on the device for a fluid supply with the concentrated fluids being proportionately mixed with the water supply inlet through a venturi device. In most cases, the operation of this device is mechanical with the solenoid valves operated electrically by the timer.

The Serfass, et al. patent (U.S. Pat. No. 3,441,136) discloses an early dialyzer reuse device in that the device provides a logic unit which programs the dialysis system through cycles of operation in which the entire system, including the dialyzer, is rinsed, sterilized and cooled with water and in which monitors are provided to test the system to verify that it meets critical parameters before a hemodialysis treatment is started. The preliminary operation provides a rinse of the system and dialyzer with water with the sterilizing operations providing a continuous flush with high temperature water. After the sterilization cycle, the entire system is again flushed with water to cool down components with the system then filled with dialysis fluid. A test cycle of the dialyzer is then performed prior to the actual dialysis treatment function.

The Hardy patent (U.S. Pat. No. 4,166,031) discloses a dialyzer cleaning apparatus which circulates cleaning, flushing and sterilizing solutions through the dialysate and blood chambers of the dialyzer in a parallel flow arrangement. The system utilizes solenoid valves to regulate and sequence fluid flow at the proper time. A venturi system is utilized to proportionately dilute and mix the cleaning and sterilizing fluids prior to passage through the dialyzer chambers.

The Mason patent (U.S. Pat. No. 3,920,030) also discloses a reuse device for cleaning and disinfecting artificial kidneys. This patent discloses the use of enclosed tubular pumps for moving the solution through the system. In addition, solenoids are utilized to pinch or close off resilient tubes for blocking the flow in certain lines. The device is designed so that the tubular manifold unit of the device can be separated and replaced with other units for different patients. Thus, each manifold unit can be maintained unique to each patient.

An article entitled "SIMULTANEOUS REPROCESSING OF HOLLOW FIBER DIALYZERS AND BLOOD TUBING SETS FOR MULTIPLE USE" by David A. Ogden, et al., and published in *DIALYSIS AND TRANSPLANTATION* magazine, Volume 13, No. 6, June, 1984, discloses a series of tests that were performed on hemodialysis machines and disposable dialyzers to determine the effect of reusing dialyzers for a number of times. The machine used during these tests was an early preliminary machine designed by the applicant which performed a similar automatic reuse function. The present invention is a decidedly patentable improvement over the earlier machine and system described in this article.

SUMMARY OF THE INVENTION

A reuse system for cleansing and disinfecting dialyzers, blood tubing sets and hemodialysis machines is provided which includes a basic automatic reuse device, a flow adapter valve and a blood tube manifold. Through the use of these devices, a completely automatic system is provided for the reuse of dialyzers or artificial kidneys and for a test certification sequence before actual reuse of the dialyzer.

In the past, various reuse devices have been provided which automatically perform a cleaning cycle, rinse cycle and sterilization cycle prior to reuse of the dialyzer. In most of these devices, the cleaning and sterilizing fluid concentrates are diluted to the proper level prior to use, and the actual time for each of the cycles can be varied somewhat as required. The present system also does this with the added feature that the cleansing and disinfecting fluid path is directed through the dialyzer in a series-counterflow arrangement. This procedure provides a reverse pressure differential across the dialyzer membrane which provides a more thorough cleansing of the "pores" of the membrane during the cleansing cycle. In addition, a much more complete flushing of the system is provided.

The reuse device is connected to a suitable source of water with additional input connections to reservoirs or bottles containing the concentrated cleansing and disinfecting solutions. The controlled fluid output from the reuse device is connected to a negative pressure or vacuum point in the dialysate pathway of the hemodialysis machine. The vacuum draws solutions from the reservoirs through the reuse device and into the dialysis machine which thoroughly dilutes and mixes prior to the cleaning, rinsing and sterilization cycles.

The electrical power for the dialysis machine is connected through the reuse device which automatically controls the primary electrical power to the dialysis machine during its operation, cleansing and reuse cycle.

The adapter valve is installed in the external tubing network of the hemodialysis machine, including a connection to the dialyzer. This valve permits the rerouting of the liquid lines depending upon the phase of the operation that is in progress without disconnecting the lines which can violate the integrity of the system by introducing contamination or bacteria.

The blood tubing manifold provides a path for flow through the peripheral pressure sensing and medication lines which are required during the dialysis process. This manifold is connected in parallel so that reliable and complete cleansing and disinfecting of these lines will be performed.

After the entire dialysis system has been disinfected through the reuse system and stored, the reuse system characterizes the dialyzer by means of a clearance test to certify the integrity of the dialyzer prior to reuse. This test is performed in a closed loop arrangement which retains the sterility of the system with no possibility of contamination. In fact, with the system of the present invention, the only break in the main blood tubing line is effected when the blood lines are connected to the patient. All other primary blood lines remain intact as well as those primary lines on the dialysate side of the dialyzer.

An interlock switch is provided on the reuse device to change over operation of the system from reuse to dialyzer test and normal operation. The actuation of the switch engages an occluding roller blocking the output line on the device to assure the integrity of the dialyzer test. This switch is primarily a safety feature, preventing solution flow through the device during testing and normal operation. The clearance test provided by this system not only validates the integrity of the dialyzer but the entire hemodialysis machine and system as well.

Operation of the reuse cycle is controlled by a suitably programmed and replaceable memory. This circuitry is bad on an internal clock which performs the automatic functions of the system. The actual status of the system during the operation and test is displayed by easily visible indicator lights.

As can be seen herein, the overall operation of the system is extremely simple and straightforward with the entire system capable of being operated by a person or patient with only minimal training. This arrangement can be easily adapted for individual use in a home setting, and also can be utilized in dialysis centers.

While it is understood that reference has been made to a specific dialyzer reuse and test system as shown and described herein, any other variations of this system which utilizes one or more of the features described herein, are to be considered part of this invention.

BRIEF DESCRIPTION OF THE DRAWINGS

Other features and advantages of the present invention will become apparent in the following detailed description of the invention wherein like reference numbers will denote the same elements in the accompanying drawings.

FIG. 1 shows a pictorial view of the system according to the present invention connected to a dialyzer and a hemodialysis machine;

FIG. 2 shows a perspective front view of the reuse device according to the present invention;

FIG. 3 shows a perspective rear view of the same device;

FIG. 4 shows a partial pictorial view of the interlock switch shown on the rear panel of the reuse device;

FIG. 5a and 5b is a block diagram showing the operational section of the reuse device;

FIG. 6a and 6b is a logic diagram showing the cleaning and disinfecting function of the reuse system;

FIG. 7a and 7b is a logic diagram showing the dialyzer test function of the device;

FIG. 8 is a perspective view of the flow adapter valve which is part of the reuse system;

FIG. 9 shows a bottom perspective view of the adapter valve handle showing the fluid recesses;

FIG. 10 is a cross-sectional view taken along lines 10—10 of FIG. 8;

FIG. 11 is a cross-sectional view taken along lines 11—11 of FIG. 8;

FIG. 12 shows a pictorial flow diagram of the flow adapter valve positioned during clearance testing and normal dialysis treatment;

FIG. 13 is a pictorial flow diagram of the adapter valve during the reuse cycle;

FIG. 14 is a pictorial flow diagram of the adapter valve which allows the flow to be intermittently reversed through the dialyzer for cleaning purposes;

FIG. 15 shows a pictorial diagram of the system connected to the dialyzer and hemodialysis machine during the reuse cleaning and disinfecting operation;

FIG. 16 is a partial flow diagram showing the adapter valve in the reverse flow configuration; and FIG. 17 is a partial pictorial view showing the adapter valve in the dialyzer test and normal dialysis configuration.

DETAILED DESCRIPTION OF THE INVENTION

Figure 5A:
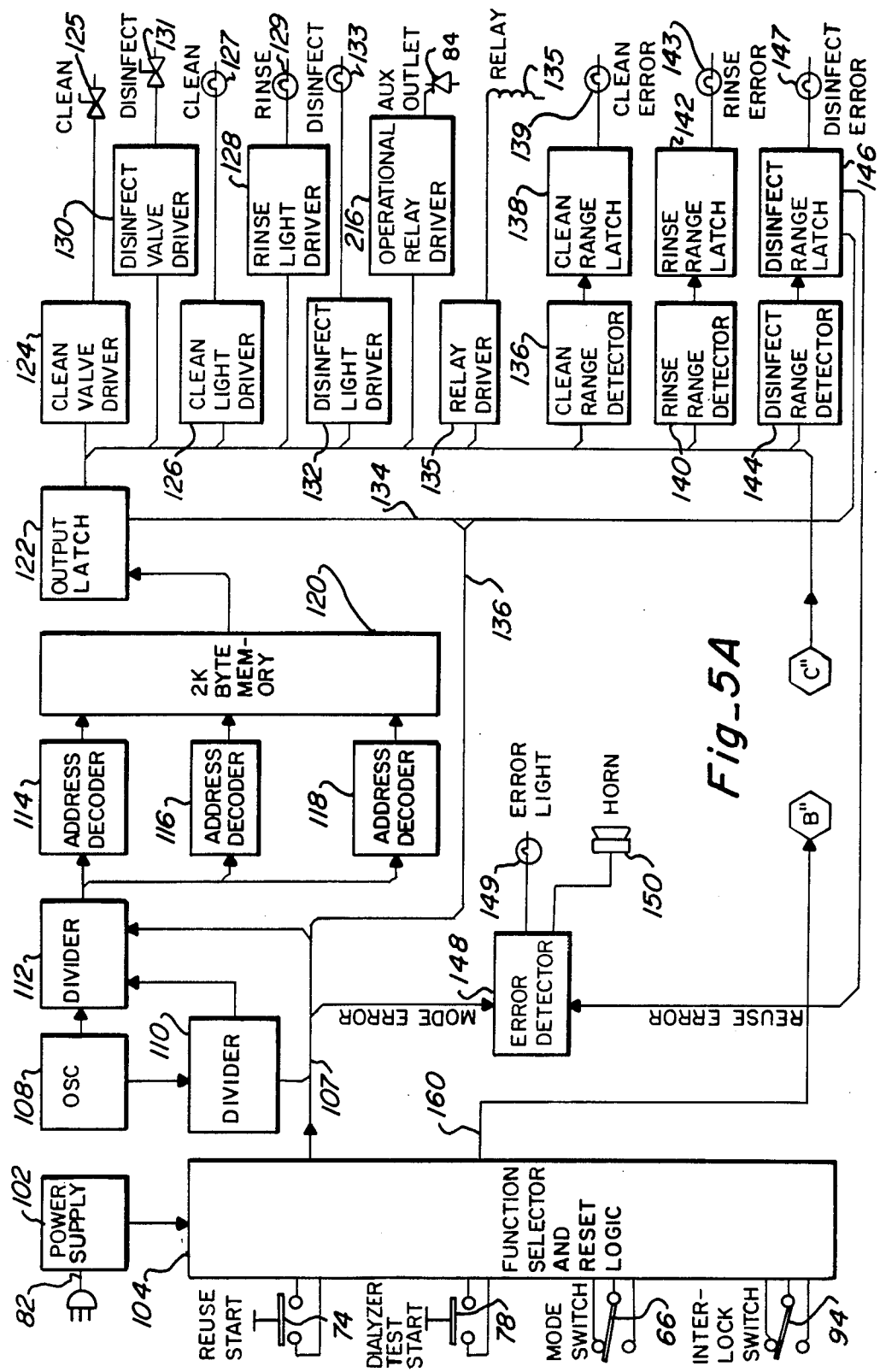

Turning now more specifically to the drawings, FIG. 1 shows a reuse system 10 according to the present invention which is semipermanently connected to a hemodialysis machine M and an artificial kidney or dialyzer D. Blood drip chambers C1 and C2 are provided upstream and downstream of the dialyzer D to control the flow of blood through the dialyzer as well as remove any air bubbles which might be present. A roller type blood pump P or some other type of suitable pump is provided on the dialysis machine M to aid in movement of the blood from the patient, through the dialyzer, and back to the patient. This same pump is also utilized during the dialyzer test cycle to circulate the fluid in the blood chamber side of the dialyzer during the clearance test as well as flushing of the diinfectant remaining in the closed loop, as will be explained later.

The reuse system 10 according to the present invention includes the reuse device 12, adapter valve 14 and blood tubing manifold 16. The reuse device 12 is connected to input tubes 18, 20 which are flow connected to reservoirs B and F, which contain concentrates of a cleaning solution and a disinfecting solution, respectively.

As is well known in the prior art, the cleaning solution can be of any suitabl solution such as sodium hypochlorite which is commonly known as household bleach. The sodium hypochlorite solution or standard bleach is of a 5.25% concentration prior to being introduced into the system. The disinfecting solution can be any suitable solution such as an aqueous formaldehyde solution having a 37% USP grade concentration plus 80 grams of sodium chloride (agent grade) and 0.4 grams FD&C blue dye per gallon. Since the formaldehyde solution is quite toxic, the blue dye is added as an identifier to indicate the presence of the formaldehyde within the system. This is a precautionary safety feature which is provided to prevent accidental introduction of the formaldehyde solution to the patient. It is also important to note that the reservoirs B and F are substantially sealed, unbreakable containers which help to minimize the release of any fumes of either the bleach or formaldehyde into the atmosphere which can be irritating or detrimental to humans.

As shown in FIG. 1, the reuse device 12 is connected into the dialysis machine M by means of the output tube 22. The output tube 22 introduces solutions of bleach or formaldehyde into the dialysis machine M in which water is continuously flowing when dialysate is not being generated. The connection of this output tube 22 is made at a negative pressure or vacuum point in the dialysate preparation and conditioning section of the machine M. After being filtered and heated to the proper temperature, the output line 24 of the dialysis machine M, which normally carries dialysate, connects directly into the inlet 26 for the dialysate chamber of the dialyzer D. Outlet 28 of the dialysate chamber is connected by tubing 30 to the dialysate input 32 of the adapter valve 14. With the handle of the adapter valve 34 in the reuse position, the flow passes through valve 14 to arterial fitting 58, tubing 60 to blood pump segment 44. The pump segment 44 is not installed during the reuse cycle. Flow continues to arterial drip chamber C1 and out bloodline 46. Arterial monitor line 47 and saline line 57 are attached to manifold 16. Branching off of bloodline 46 is the heparin line 59 which is also attached to manifold 16. Flow goes into the blood side of the dialyzer D through arterial fitting 48, out through venous fitting 50 and into the venous drip chamber C2 by bloodline 52. The venous monitor line is connected to manifold 16 thus providing the parallel pathway through the manifold 16. Flow continues through bloodline 54 into venous connection 56 on adapter 14. The flow is routed through to fitting 35, tubing 36, tee 38 and conductivity sensor 42 and effluent drain line 40. The conductivity sensor is electrically connected by suitable wires to the reuse device 12.

During a clearance test of the dialyzer, the fluid in the blood chamber of the dialyzer is recirculated in the blood tubing closed loop. This closed loop consists of the tube 44 which is part of the blood tubing set which is positioned within the blood pump P provided on the dialysis machine M which in turn is connected to the drip chamber C1, tube 46 and the arterial blood connection 48 on the dialyzer D. Coming off the dialyzer D at the venous blood connection 50 is tube 52 which is connected through the venous drip chamber C2 and tube 54 to the venous blood connector 56 on the adapter valve 14. With the handle in the proper position flow goes directly across the valve to arterial fitting 58, through tube 60, to the blood pump segment 44, completing the blood side loop.

The outside configuration of the reuse device 12 is shown in FIGS. 2 and 3. The novel reuse device 12 includes an outside cover 64, a front panel 65 and a back panel 67. The front operational panel 65 has a mode selection switch 66 to set the operation of the device either in the reuse or dialyzer test function. The remaining portion of the front panel 65 is divided into sections 70 and 72 which are catagorized for the two operational functions. The reuse section 70 includes "start" push switch 74 and test status indicator lights 76. By the same token the dialyzer test section 72 includes the "start" push switch 78 and indicator lights 80. Each of the indicator lights 76 and 80 are of a different color with its function printed just below on the front panel 65.

The back cover 67 of the reuse device 12 includes apertures for the electrical power cable 82 and auxiliary power outlet 84. The power cord from the associated hemodialysis machine M is connected to the auxiliary power outlet 84 so that the "on-off" operation of the machine can be controlled by the reuse device. Suitable fuse holders 86 are provided in the power supply portion of the device to protect the electrical components of the system. Moving to the right of the fuses 86 is the cable or wires 88 for the conductivity probe 42. Immediately below the probe connection is an accessory control receptacle 90 and three voltage test connectors 92 to which a volt meter or other test equipment can be connected to provide a visual readout of the conductivity and temperature of the fluids. The accessory control receptacle is wired to an internal relay to control various functions within the hemodialysis machine, as desired.

On the extreme right side of the panel 67 are apertures for entrance of the bleach tube 18, formaldehyde tube 20, water tube 21 and fluid outlet tube 22. The incoming water line 21 is connected to a suitable continuous source of filtered water. This source can conveniently found in the hydraulic section of the dialysis machine M to which the line 21 can be connected.

An important feature of the present invention is the interlock switch 94 which provides both an electrical switching as well as a mechanical valving function. An eccentrically located roller 100 is provided on the operating knob 95 located 90° from the function designating arrow. The output fluid tube 22 from the reuse device 12 is routed over a bracket 96 which has a flat upper surface 98 and clamps 99 which hold the flexible tube 22 in rigid position adjacent to the outer circumferential surface of the knob 95.

As shown in FIG. 4, as the knob 95 is rotated to the dialyzer test position, the roller 100 is brought into close proximity to the upper surface 98 of the bracket 96 which completely pinches off or occludes the output tube 22. This is a safety device which prevents any flow of liquid from the reuse device 12 during the dialyzer test function or during normal dialysis treatment. In this way, the clearance test, as will be discussed later, is completely isolated from the reuse device to be certain that the results of the test are accurate and reflect the true condition of the dialyzer.

FIG. 5 shows a block diagram of the operations of the reuse device 12 according to the present invention. Power plug 82 is connected to a 115VAC, 50-60 HZ source of electrical power. The power supply 102 provides power to operate the electronic circuitry as well as the fluid control valves and indicator lights. Power is fed from the power supply 102 to the internal logic device 104 which provides the selector-logic functions for the operation of the reuse device 12. Mode switch 66 which is found on the front panel 65 and interlock switch 94 which is controlled by knob 95 on the rear panel 67 are electrically connected to the function selector and reset logic device 104.

It is mandatory for proper operation that both the mode switch 66 and the interlock switch 94 be in the equivalent electrical position either for the reuse function or the dialyzer test function.

Depending upon the mode selected, either the reuse start push button switch 74 or dialyzer test push button switch 78 located on the front panel 65 is actuated to start the desired function.

Oscillator 108 and dividers 110 and 112 generate a system clock. The time base for the error lamp 149 and horn 150 is a product of the system clock. The system clock is divided further to generate time base for the duration of each portion of the reuse cycle. The output signal from the divider 112 is fed to the address decoders 114, 116 and 118 which, in turn, sequentially retrieve the data instructions from the memory 120, which has been programmed to control the operation of the reuse cycle. The output commands of the memory 120 directly access the appropriate external function drivers 124, 126, 132, 134, 130, 128 and 216. In proper sequential order, the clean valve driver opens the clean valve 125 and simultaneously, the clean light driver 126 energizes the clean light 127. The energizing of the bleach control valve allows bleach to be drawn through the device and into the output tube. This output solution of bleach passes from the output line 22 to the input of the hemodialysis machine M where it is mixed with the machine water flow to obtain the desired level of dilution.

Once the cleaning cycle timing has been completed, the memory 120 switches the clean valve driver and thus deactivates the bleach control valve. Simultaneously, the clean range detector 136 is activated. This range detector is programmed to check the conductivity of the cleaning cycle fluid and if it is not within predetermined limits, the detector actuates the clean range latch 138, the clean error LED 139, the error lamp 149 and the horn 150.

At this time, the rinse light driver 128 is energized causing the rinse light to be illuminated. The cycle continues to the end of rinse at which point the rinse cycle range detector 140 is activated. If the predetermined parameters of conductivity are not met, the rinse range latch 142 is activated causing the rinse error LED 143, the error lamp 149 and the horn 150 to be activated.

Upon completion of the timing of the rinse cycle, the disinfect valve driver 130 is energized which activates the formaldehyde control valve 131 permitting the highly concentrated disinfect solution to be drawn through the output line 22. Simultaneously, the disinfect light driver 132 and disinfect indicator light 133 are energized.

At the end of the disinfect cycle, the disinfect range detector 144 is activated. Failure of the disinfect solution conductivity to be within the predetermined range actuates the disinfect range latch 146 energizing the error LED 147, the error light 149 and the horn 150. It is to be noted that when any of the error functions have been activated, the remaining functions of the device are not interrupted.

The last stage in the reuse cycle is a short delay, about a minute, allowing the water to rinse the formaldehyde from the output line 22. At this point all drivers are deactivated allowing the device to appear idle. In this "resting" condition, water continues to flow through the device providing for an internal rinse of valves and other components. After this delay has been completed, the clean light driver 126, the disinfect light driver 132 and the rinse light driver 128 are activated causing the respective lights 127, 133 and 129 to be illuminated. Also at this time the operational relay driver 216 is deactivated shutting off power to auxiliary outlet 90 and thus the dialysis machine.

When the mode switch 66 and interlock switch 94 are both in the dialyzer test position, a second major function of the reuse device is readied. After pushing the dialyzer test start switch 78, the test function is automatically initiated. A counter 162 waits for a certain number of pulses from the oscillator 164 which establishes a predetermined test cycle period. Once the proper conductivity level is reached, the counter is started and the run light driver controller 166 illuminates the run light 167.

The temperature and conductivity probe 42 is connected to a temperature compensated circuit whose voltage output is proportional to conductivity. The signal is electrically doubled and then fed as input to range detectors. Just prior to the doubling stage is a test point 92a which provides a readout signal of the conductivity. Another test point 92b is also provided for readout of the temperature.

The initial range detector initiates the operation of the run light during the test cycle. When the conductivity output from the probe 42 reaches a predetermined minimum value, the test timing is automatically started and the conductivity output is monitored continuously. If the conductivity reading rises into a required minimum range prior to the end of the predetermined time period for the test, the pass range detector initiates the pass range latch 197 which energizes the pass light driver 198 and pass light 199. On the other hand, if the conductivity does not reach the required minimum range by the end of the test run, the fail range detector output signal energizes the fail range latch 202 which initiates the fail light driver 204 and the fail light 206. At the same time the output signal from the fail range detector 196 is fed to the fail direction detector 208 which differentiates whether the conductivity reading was above or below the required predetermined range which initiates the fail direction latch and either the low light driver 211 and light 212 or the high light driver 213 and light 214. In this way if the dialyzer clearance test has failed, the user will have an indication as to what condition caused the failure of the dialyzer. In actual operation, the test time is started when the dialysate leaving the dialyzer reaches a conductivity of 6 millimhos and the conductivity must reach a range of 8.5 to 11.0 millimhos within a time period of 22 seconds.

The diagrams illustrated in FIGS. 6 and 7 show the logic process performed by the circuit in accomplishing the reuse and dialyzer test procedures. In FIG. 6, the reuse cycle of the device is described. The steps in this logic sequence follow the same general pattern as previously discussed in the block diagrams. The entire cycle for the reuse operation is initiated by the start switch function. At this point, both the interlock switch and the mode switch are checked to make sure that they are in the reuse position. If either one is not, the cycle cannot be started until the switches are set in the proper position. Once the cycle is started, the start light within the switch 74 is illuminated, the bleach control valve is opened, and the cleaning cycle is started. The time for the cleaning cycle is monitored, and the cleaning process continues until the pre-set time period is completed. Once this time has expired the cycle ends, the cleaning lamp and bleach control valve are de-energized and a check is made of the conductivity of the fluid downstream of the dialyzer. If this conductivity at this time is out of the desired predetermined range, an error function is initiated with the error light and error signal horn or beeper initiated.

Regardless of an error signal, the rinse cycle is then initiated. During this cycle, the time is monitored and upon expiration, a second conductivity check is made to determine if the conductivity of the fluid flow now present is within the proper range. If the fluid is out of range at this point the error light 149, the horn 150 and the water error LED 143 are initiated. Again, the process will continue regardless of an error signal.

A third conductivity check is performed at the end of the disinfect cycle. If the conductivity is out of the predetermined range, indicating that the concentration or substance of the disinfectant is in error, the error light and signal beeper are promptly initiated.

Upon determination that the disinfecting process has been completed, a short time delay is provided. This time delay allows the output line to be rinsed of formaldehyde. After the delay the solid state relay is de-energized shutting off power to auxiliary outlet 90. The memory 120 sends a signal to turn all status lights (126, 129, and 133) on and to a 5-volt relay 135, opening at least a pair of contacts.

The entire dialysis system, including the dialyzer, blood lines, hemodialysis machine and reuse device, is left intact for storage; thus, the disinfecting solution remains in the entire system during the storage period which maintains the sterility of all components and tubes and prevents contamination or growth of any bacteria.

As the need arises, and it is desired to use the dialyzer and hemodialysis machine again for patient treatment, the adapter valve 14 is turned so as to place the valve in proper position for the normal patient dialysis treatment. This isolates the dialysate chamber and tubing of the dialyzer from the blood chamber and tubing. Thus, the dialyzer blood tubing forms a closed loop which still contains the disinfectant solution, such as the 4% solution of formaldehyde.

Thus, the dialysate side of the dialyzer and its associated tubing is connected directly to the output of the hemodialysis machine. In the machine, concentrated dialysate is being diluted, conditioned and allowed to temporarily bypass to the drain to allow the dialysate flow to stabilize with the proper concentration and temperature. Once the system has stabilized, the dialyzer clearance test can begin.

This test as shown in FIG. 7 is initiated by verifying that the interlock switch 94 provided on the back panel of the device 12 is in the proper position for the test mode with the output line 22 from the device blocked or closed. In addition, the mode switch 66 on the front panel is also verified to be in the dialyzer test position. With both switches in the correct position, the push button start switch 78 for the dialyzer test is initiated. Simultaneously, the dialysate from the hemodialysis machine M is switched to flow through the dialyzer and the blood pump is started to circulate the fluid in the blood tubing closed loop. The conductivity of the dialysate is monitored continuously. When the conductivity of the dialysate rises to the correct reading, the timer in the reuse device is initiated. The conductivity of the dialysate leaving the dialyzer is monitored and must reach a desired range before the timer completes the predetermined cycle. If the conductivity before the end of the time period is within the predetermined range, the dialyzer is considered to be satisfactory and has passed the clearance test. At this point, the pass light is turned on and the test is completed. If, however, the conductivity is out of the desired range, the fail light is initiated and either the or low fail light is also initiated depending upon the actual conductivity reading. In this way, the user is made aware that the dialyzer has failed the test with the additional information as to the condition of the dialyzer membrane. At this point, the test is completed.

Disinfectant solution still remains in the blood tubing circuit. While dialysate continuously flows through the dialysate chamber of the dialyzer, the disinfectant solution is recirculated through the blood tubing lines. With molecular transfer across the dialyzer membrane, the disinfectant is transferred across the membrane where it is disposed with the dialysate. This process continues until complete flushing is accomplished.

After flushing, the condition of the fluid within the blood lines is visually checked to make sure that the disinfectant or formaldehyde solution containing a blue dye indicator has been completely removed from the system. Once this has been visually verified, a chemical test is performed to verify that no formaldehyde or disinfectant residual solution remains in either side of the system. Once the flushing process has been completed and verified, the blood line can be separated and connected to the patient for the treatment process.

The adapter flow valve 14 which permits the rerouting of the flow path during the reuse and dialyzer test cycles is shown in FIG. 15. The adapter valve 14 includes a body 230 which can be molded or cast or machined usually from a solid block of material. A handle 34 mounted on top of the body 230 permits the actual switching of the flow path through the valve. The handle 34 has an elongated ridge 35 which extends diametrically across the upper surface. This ridge is provided as a finger grip to facilitate the rotation of the handle 34 in switching the valve 14. A drilled bore 232 is provided in the handle 34. A cap screw 233 is positioned through the aperture 232 and engaged with the threaded aperture 234 provided in the center of the body 230. An O-ring 236 is provided under the head of the cap screw 233 to seal the internal cavity provided on the underside of the handle.

The underside of the handle 34 has an elongated central recess 238 and two oppositely spaced recesses 240 and 242, respectively. The aperture 232 penetrates through the elongated cavity 238 thus necessitating the seal or O-ring 236. An O-ring groove and O-ring 244 are provided around the entire perimeter of the under surface 237 of the handle 34. In a like manner, O-ring seals 246, 248 and 250 are positioned around the perimeter of the recesses 240, 242 and 238, respectively. These seals are also spaced slightly from the edge of the recesses to provide suitable O-ring grooves for sealing purposes. With the handle 34 held in position with the capscrew 233, the O-rings seal against the surface 231 and prevent crossover or leakage of the fluids between the recesses.

The input dialysate line 32 is connected to the body of the valve 14 by a tube fitting 260 mounted in the threaded aperture 262. The threaded aperture is connected to the top surface 231 of the valve body 230 by a drilled L-shaped passageway 264. In the same way the dialysate output line 36 is joined to the valve by means of the fitting 266, mounted in the threaded aperture 268. The threaded aperture 268 is, in turn, connected to the top surface 231 by means of a drilled L-shaped passageway 270. The openings of the passageways 264, 270 in the surface 231 are located diametrically opposite each other and equal distant from the center tapped hole 234. In addition, the radius of these openings matches the diameter of the elongated recess 238. In this way, with the elongated recess diametrically aligned along the longitudinal axis of the body 230, the input and output dialysis lines 32, 36 have a common flow path through the recess 238.

Blood line connectors 56, 58 are mounted on opposite sides of the valve body 230 on an axis which is through the body center aperture and 90° to the axis between the dialysate lines 32, 36. The blood fitting, is mounted on the side of the valve body 230 in a threaded aperture 280 which, in turn, is connected to a drilled passageway 282. The venous blood fitting 58 is threadably mounted in the aperture 284 which, in turn, is connected by an angled drilled passageway 286. The ends of the passageways 282, 286 communicate with the top surface 231 of valve body 230 which correspond to the cavities provided by the recesses 240, 242, respectively. These openings are also spaced the same radius from the center threaded aperture 234 as the openings to the dialysate passageways. Thus, all four of the openings align on a circle having an equal radius from the center aperture of the valve body. the recesses 238, 240, 242 are shaped so that the handle 34 can be rotated 45° in either direction from center which will change the flow path from a straight-through dialysate flow to one where the input from tube 32 and output from tube 36 can be alternately switched between the arterial and venous tubes.

Pin 290 is mounted so as to protrude from the upper edge of the handle 34 in alignment with the ridge 35. A pair of stop pins 292, 294 are positioned at 45° angles from the center position and adjacent to the outer circumference of the handle 34. In this way the pin 290 and the stops 292, 294 prevent the handle 34 from being rotated beyond the 45° position in either direction to restrict rotation of the handle 34 and limit the adapter valve to the three desired flow path positions. It is also possible to provide a detent mechanism in the handle to supplement or replace the stop-pin 290.

In order to allow some flow between the blood arterial and venous fittings 56 and 58 when the valve is in the position illustrated for normal dialysate flow, a passageway 296 having a diameter of approximately 0.04 inches is provided to allow continuous bypass flow between the blood fittings 56, 58 when the blood lines are in a closed loop for flushing and testing. FIG. 12 illustrates the flow path of the adapter valve 14 with the handle shown in the center or normal position of FIG. 12. In this arrangement, the flow is directed in through the line 32 and out through the line 36. The flow between fittings 58 and 56 is blocked except for the bypass line 296.

FIG. 13 illustrates the flow path of the adapter in ithe reuse position. Flow is through input line 32 and out through blood arterial fitting 56. This goes through the blood side loop and into fitting 58, then out through fitting 36. With the handle turned in the opposite position, the flow is through the fitting 32 and out through the venous fitting 58, through the blood side loop and then into the arterial fitting 56 and out through fitting 36. As will be explained in the operation of the system, the adapter valve position shown in FIG. 12 is utilized during the dialyzer test and normal dialysis treatment process. The arrangement shown in ia FIG. 13 is commonly used during the reuse process when cleaning and disinfecting the dialyzer system. The position shown in FIG. 14 causes the reversal of the flow through the dialyzer and blood tubes during the cleaning and disinfecting process in order to better clean and remove clots and other debris which might be lodged in the tubing. Thus, alternating reverse flow can be obtained by switching back and forth between the positions shown in FIGS. 13 and 14.

OPERATION

The reuse system, according to the present invention, primarily includes the reuse device 12, the adapter valve 14 and the blood tubing manifold 16. Once the dialysis treatment has been completed on the patient, a rinse back procedure is provided to remove much of the blood which is present in the blood tubing set and return the blood to the patient.

In most cases, the reuse device 12 is permanently or semi-permanently connected into the dialysis machine system and is intended to remain connected during further use.

In the same manner, the adapter valve 14 is also connected into the dialysate and blood lines of the hemodialysis machine and allowed to remain connected during all operations. Once the rinse back procedure has been accomplished and the blood tubing has been disconnected from the patient, the ends of the blood lines are connected to the blood connector fittings 56, 58 on the adapter valve 14. At the same time the blood pressure lines 47, 49 and heparin injection line 51 and medication line 53 are connected to the ports of the manifold.

FIG. 15 shows the flow diagram of the overall system during the reuse cycle. The main inlet power cable from the hemodialysis machine is connected to the auxiliary power receptacle 84 on the reuse device 12. The output tube 22 from the reuse device is connected to a tee 302 at a low pressure vacuum point in the internal dialysate tubing 304, 306 within the hemodialysis machine M/ An air removal pump 308 de-airs the dialysate which flows into dialyzer D by connector 26.

It is to be understood that the tubing connection and arrangements shown in FIG. 15 are essentially the same as those shown in FIG. 1 with the exception of the blood line 44 mounted within the blood pump P. Thus, the transition between the different processes can be easily made without breaking or disconnecting primary tubes or fittings to accomplish the overall purpose. The reuse cleaning flow from the dialysate machine to the system is usually set at 500 milliliters per minute.

With the mode and interlock switches in the reuse position, the reuse process is initiated by pushing the reuse start button. With the dialysis machine internal pump operating, concentrated bleach (5.25% solution) is drawn from the reservoir B and enters the dialysis machine through tee 302. In the dialysis machine, this solution is mixed with the water flow to dilute it to the proper percentage of concentration (0.25%). This solution then passes through the air removal pump 308, through the dialyzer D and out through the connector 28 and to the adapter valve 14. The cleaning solution passes through the valve 14, blood fitting 56 and blood tube 54 where it flows upward through the venous drip chamber C2 and then through the dialyzer D. This flow is counter to the normal flow of blood through the dialyzer. After passing through the dialyzer, the cleaning solution flows through the arterial drip chamber Cl returning to the adapter valve through the connector 63 and edication fittings 61, 62. The flow crosses over the adapter valve and out through the line 36, conductivity probe 42 and drain line 40. The conductivity of the fluid is measured by the probe 42 to verify that the proper solution is being used during the various stages of the cycle.

Since the inside diameters of the secondary blood lines such as medication tubes 51, 53 and pressure lines 47, 49 are quite small, connections are made from the tee's 61, 62 through secondary tubes and through the manifold 16 to allow the solution to flow through these tubes to provide a flushing action during the cleaning process. To promote flow, it may be necessary to open and close the manifold valves momentarily or reverse the crossover position of the adapter valve 14 as shown in FIG. 14 to pulse or reverse the flow through the lines to aid the cleaning process.

The reuse device times the cleaning cycle for approximately twenty minutes and then automatically switches to a water only flush cycle for approximately five minutes. In this mode, the bleach is shut off and the normal water flow through the reuse device and machine is used to rinse the entire system for the desired time period. At the end of the rinse cycle, a disinfecting solution, such as concentrated formaldehyde (37% solution) is drawn from the reservoir F. This solution then passes into the machine where it is diluted to a concentration of approximately 4%. This solution then passes through the system tubing in the same flow path as previously described for a period of approximately eight minutes. After this time period, the disinfectant flow is stopped, and a minute delay is provided during which water flows through the device allowing for a rinseout of the output line 22 of formaldehyde. The hemodialysis machine M is switched off via receptacle 84, preventing the disinfect solution from being rinsed out of the machine. In this way, the dialyzer, blood lines and hemodialysis machine are filled with the disinfectant solution, and this solution remains in the entire system during the nonuse or storage period.

During the reuse process, the conductivity probe checks, at the end of each stage of the cycle, the conductivity of the fluid passing through the system. The conductivity during the cleaning process must be within range of six to twelve millimhos. During the water rinse cycle, the conductivity will drop to the range of zero to two millimhos. Following this and during the formaldehyde introduction to the system, the conductivity will again rise to approximately two to six millimhos. In this way it is possible to identify and verify that the proper solution is being routed through the system during its proper timed cycle. This is especially important during the disinfecting cycle to verify the presence of the disinfectant to maintain the sterility of the system during the nonuse or storage period. This is a primary verification test in addition to the secondary visual observation of the blue color of the disinfecting solution due to the presence of the added dye.

After the storage period and in preparation for the next dialysis treatment, the reuse device is switched to the "Dialyzer Test" mode which rests the system and applies power to the hemodialysis machine M. The dialysis machine is switched to a "rinse" mode, and the machine concentrate line is dropped in concentrate allowing the machine to produce dialysate. The machine is also in the "bypass" mode to avoid flowing dialysate fluid past the dialyzer prior to the test. The adapter valve is switched to the "normal" dialysis position at this time. This separates the two fluid flow paths through the dialyzer. The blood pump section is placed into the blood pump P. This is easily done by allowing the pump to run for a couple of revolutions and feeding the tubing from one end of the pump. The pump, however, must not continue to run at this time. Once the dialysate has stabilized at the proper concentration and temperature, the system is ready for a dialyzer clearance test.

The start switch 78 for "Dialyzer Test" is depressed, illuminating the start lamp and initiating the dialyzer testing function. The dialysis machine M flow rate is preset at 500 milliliters per minute and the blood pump flow rate is set at 200 milliliters per minute. Simultaneously, the dialysis machine M is taken out of "bypass" and the blood pump is turned on. There is now two separate fluid paths: the blood side of the dialyzer and the blood tubing set; and the dialysate flow through the dialysate side of the dialyzer, through the adapter, through the conductivity probe 42 and then to the drain. A loop is completed for the blood side path by the bypass line 296 in the adapter valve 14. Thus, a counter-current flow is established, "dialyzing" formaldehyde from the blood side and electrolites from the dialysate side. This reduces the effluent dialysate conductivity (concentration).

Once the conductivity of the effluent dialysate reaches 6.0 millihos the timed test period is initiated. A stable condition will be reached in a short time, during which the conductivity must be in a range of 8.5 to 11.0 millimhos for a satisfactory pass of the dialyzer's clearance. If the conductivity at the end of the time period is either too low or too high, the fail light on the reuse device is automatically illuminated along with the light indicating the high or low condition. A high conductivity reading indicates that the dialyzer clearance is low. A low conductivity reading means that the dialyzer may have a leak across the membrane, which would be unsatisfactory during the dialysis treatment. In either case where the test has failed, it is necessary to replace the dialyzer with a new unit prior to the patient treatment.

If the clearance test is passed, the dialysate flow is continued for a period of twenty-two to thirty minutes and the blood pump operation is continued. In this way, the formaldehyde fluid remaining in the blood tubing is recirculated and dissipated across the dialyzer membrane at the same time saline solution is added to the blood side to replace the volume of fluid lost. This process continues until the formaldehyde has been completely removed from the blood lines. At the end of this cycle, a chemical test is made on the fluid in both the blood side as well as the dialysate side of the dialyzer to verify that no formaldehyde is present in either system. Once this verification has been made, the dialyzer, blood lines and hemodialysis machine are ready to be used for dialysis treatment of the patient.

It is to understood that one of the important features of the reuse system as described herein is that only a minimum number of tubing connections are broken and reconnected hen the entire system is being changed over from the reuse cycle to the normal dialyzer treatment cycle. In actuality, the blood line connections 56, 58 are the only primary tubes which must be disconnected and reconnected to the patient. At the same time, the only other connections which need to be disturbed are the auxiliary or secondary blood lines on the machine such as the drip chamber lines 47 and 49 and medication injection lines 51 and 53. These lines are reattached to the proper connections on the hemodialysis machine M for the proper functioning of the machine. In this way the integrity and sterility of the blood tubing set is maintained as completely as possible.

While a new and novel dialysis reuse system has been shown and described in detail in this application, it is to be understood that this invention is not to be considered to be limited to the exact form disclosed, and changes in the detail and construction of the invention may be made without departing from the spirit thereof.

What is claimed is:

1. A reuse device for automatically cleaning, disinfecting and testing a hemodialysis machine, dialyzer and blood tubing set when connected together as an operational dialysis system, the reuse device comprising:
(a) a power supply connected to a suitable source of electrical power;
(b) fluid tubing means having valve means for controlling fluid flow through the device;
(c) a pair of reservoirs of concentrated cleaning solution and disinfecting solution connected to the valve means in said tubing means;
(d) a logic circuit means connected to said power supply and having a connected read only memory storage means which has been programmed to perform a desired reuse operation cycle;
(e) said logic circuit means having input means for initiating the start of the operation cycle of the reuse device and output means connected to a control means;
(f) a control means being sequentially driven by the logic circuit means to select and drive a plurality of suitable latching circuits and indicator means for operating the valve means for controlling the flow of cleaning and disinfecting fluids at the proper time during the cycle so that the concentrated solutions will be drawn from the device to provide desired fluids to the dialysis system during the sequentialy operation of the reuse device whereby the fluid can be diluted and used to clean, rinse and sterilize the entire dialysis system; and
(g) a conductivity sensing means which senses the conductivity of the fluid leaving the dialyzer system for verifying the integrity of the dialyzer and the presence of the correct fluid in the system during the respective operational cycle of the reuse device.

2. A reuse device as defined in claim 1 wherein the device includes a timing circuit which is used in conjunction with the output of the conductivity sensing means whereby the output of the logic circuit means can perform a timed functional test of the dialyzer to determine its clearance for reuse in patient hemodialysis treatment.

3. A reuse device as defined in claim 1 wherein an interlock switch is provided on the device for selecting a reuse or dialyzer test cyclc from the logic circuit means, and the interlock switch includes a support means test for mounting and holding a portion of the output fluid tube from said reuse device and a cam means provided on said interlock switch so that when the switch is moved to the dialyzer test operation, the cam means will engage and block the output tube so as to prevent any fluid flow from the reuse device during the dialyzer test of normal use operation.

4. A reuse device as defined in claim 3 wherein said interlock switch means includes a round control handle and the support means positions the output tube at a point adjacent to the outer surface of the control handle, the cam means being a biased roller means mounted in the edge of said handle and positioned so that when the handle is turned to the dialyzer test position the roller means will be in direct contact with the output tube so as to close said tube.

5. A reuse system for the in-vitro cleaning, disinfecting and testing of a hemodialysis machine, blood tubing set and dialyzer all connected together as a dialysis system and while maintaining the sterility and integrity of the system, the reuse system, comprising:
(a) a reuse device connected to a suitable electrical power source and a source of water, concentrated cleaning solution and concentrated disinfecting solution, said reuse device including means for generating the operational fluids for cleaning and disinfecting the system and timing means for controlling the cyclic flow of these fluids through the dialysis system;
(b) adapter valve means connected to a dialysate line of the hemodialysis machine and the blood tubing set of the dialysis system whereby the fluid flow through the system can be controlled during the cycling of the reuse device, said adapter valve means is connected to the dialysis system and the valve means can be moved between a first position wherein the fluid through the system is normal for the dialysis operation, and a second position which switches the system fluid flow so that it flows in series through both the dialysate and blood chambers of the dialyzer and in a direction which is counter-current to the normal blood flow through the blood chamber to remove any clots or particles that may remain in the dialyzer;
(c) blood tubing manifold means to interconnect auxiliary tubes of the blood tubing set whereby the operational fluids during reuse will flow through all tubes of the blood tubing set so as to clean and disinfect the entire dialysis system; and
(d) the reuse device includes a condiuctivity sensing means which senses the conductivity of the fluid leaving the dialyzer system for verifying the integrity of the dialyser and the presence of the correct fluid in the system during the respective operational cycle of the reuse device.

6. A reuse system as defined in claim 5 wherein the output tubing the reuse device is connected to the hemodialysis machine at a dialysate tubing connection which is under negative pressure so as to provide the moving force for drawing concentrate fluid through the reuse device.

7. A method for cleaning and disinfecting a hemodialysis system including a hemodialysis machine, a blood tubing set and dialyzer for subsequent reuse, the cleaning and disinfecting of the system being accomplished by the use of an automatic reuse device, the steps including:
(a) connecting a fluid output of the automatic reuse device having a source of water and cleaning and disinfecting fluids to a negative pressure point in the dialysate tubing of the hemodialysis machine;
(b) connecting a fluid flow adapter valve in the hemodialysis system so that the dialysate tubes and blood tubes can be switched to allow the water, cleaning and disinfecting fluids to flow in separate paths during normal dialysis operation or in a connected series flow path during the cleaning and disinfecting operation of the dialysis system;
(c) switching the adapter valve to the series flow path;
(d) operating the reuse device to flow cleaning and disinfecting fluid in sequence through the existing hemodialysis system whereby the system, including the blood tubing set and dialyzer, is cleansed of foreign matter and disinfected;
(e) de-energizing the reuse device and hemodialysis system with residual disinfecting fluid still in the system to store the entire system intact to prevent contamination and maintain sterility of all connected components; and (f) sensing the conductivity of the fluid leaving the system for verifying the integrity of the dialyzer and the presence of the correct fluid in the system during the respective steps.

8. A method of reusing a hemodialysis system as described in claim 7 which further includes:
  (a) switching the fluid flow adapter valve to the normal operation flow path which isolates the blood tubing set into a closed loop; and
  (b) flowing dialysate from the hemodialysis system through the dialysate chamber of the dialyzer and tubing and simultaneously pumping the residual disinfecting fluid through the closed loop tubing so as to flush the disinfecting fluid through the membrane of the dialyzer so that it can be disposed of in the flowing dialysate without disconnecting or invading the fluid tubing set or dialyzer of the dialysis system.

9. A method of reusing a hemodialysis system as described in claim 8 wherein the dialysate flow rate is set at approximately 500 ml/min. and the fluid flow rate in the blood tubing set is adjusted to approximately 200 ml/min.

10. A method of reusing a hemodialysis system as described in claim 8 which further includes the step of measuring the conductivity of the dialysate during a predetermined time period at the beginning of the flushing of the disinfecting fluid and comparing the conductivity of the fluid at the beginning and end of the time period to test the dialyzer.

11. A method of reusing a hemodialysis system as described in claim 7 which further includes the step of periodically measuring the conductivity of the fluids flowing in the dialysis system to verify that the correct fluid is present during each phase of the operation.

12. A method of reusing a hemodialysis system as described in claim 7 which further includes the step of providing a manifold connector and connecting all of the tubes of the blood tubing set to the manifold connector whereby the cleaning and disinfecting fluids will be forced to flow through all of the tubes of the tubing set.

* * * * *